United States Patent
Okamoto et al.

(10) Patent No.: US 8,030,618 B2
(45) Date of Patent: Oct. 4, 2011

(54) PELLET FOR USE IN SPECTROMETRY, METHOD OF PREPARING THE SAME, AND METHOD OF SPECTROMETRY

(75) Inventors: Masashi Okamoto, Kyoto (JP); Yuichi Ogawa, Miyagi (JP)

(73) Assignees: Arkray, Inc., Kyoto (JP); Tohoku University, Miyagi (JP)

( * ) Notice: Subject to any disclaimer, the term of this patent is extended or adjusted under 35 U.S.C. 154(b) by 21 days.

(21) Appl. No.: 12/733,788

(22) PCT Filed: Sep. 25, 2008

(86) PCT No.: PCT/JP2008/067303
§ 371 (c)(1),
(2), (4) Date: Mar. 19, 2010

(87) PCT Pub. No.: WO2009/041504
PCT Pub. Date: Apr. 2, 2009

(65) Prior Publication Data
US 2010/0243901 A1 Sep. 30, 2010

(30) Foreign Application Priority Data
Sep. 25, 2007 (JP) ................................ 2007-246670

(51) Int. Cl.
*G01N 21/31* (2006.01)
(52) U.S. Cl. ................................. 250/370.09
(58) Field of Classification Search ............... 250/252.1, 250/339.07; 252/408.1, 582; 264/109; 436/164, 436/166, 171, 173
See application file for complete search history.

(56) References Cited

U.S. PATENT DOCUMENTS

| | | | |
|---|---|---|---|
| 5,470,757 A * | 11/1995 | Gagnon et al. | 436/164 |
| 6,005,027 A * | 12/1999 | Guillet et al. | 523/209 |
| 6,830,717 B2 | 12/2004 | Kopaciewicz et al. | |

FOREIGN PATENT DOCUMENTS

| | | |
|---|---|---|
| JP | 05-232018 A | 9/1993 |
| JP | 10-036686 A | 2/1998 |
| JP | 11-166891 A | 6/1999 |
| JP | 2000-214973 A | 8/2000 |
| JP | 2000-515066 A | 11/2000 |
| JP | 09-101263 A | 4/2007 |

OTHER PUBLICATIONS

Masahiko Tani et al., "Terahertz Denjiha Pulse o Mochiita Seitai Bunshi Bunko", vol. 15, No. 1, pp. 9-14, Optical Alliance (Jan. 1, 2004).
International Search Report mailed on Jan. 6, 2009.

* cited by examiner

*Primary Examiner* — David P Porta
*Assistant Examiner* — Marcus H Taningco
(74) *Attorney, Agent, or Firm* — Rader, Fishman & Grauer PLLC

(57) ABSTRACT

A pellet 4 for use in spectrometry includes a first powder 41 of a light transmitting material in a compression-molded form, and a second powder 42 which is hydrophilic and water-insoluble and is dispersedly mixed in the first powder. A sample 40 to be subjected to spectrometry is e.g. in a powdery form and dispersedly mixed in the first and the second powders 41 and 42. When the sample 40 is a hydrate, the second powder 42 exerts the effect of accelerating dehydration of the sample 40, so that stable spectrum data on the sample in the dehydrated state is obtained early. This makes it possible to perform a processing such as identification of the sample 40 early and precisely.

11 Claims, 7 Drawing Sheets

Experimental Example 4 of the Invention
PE-silica mixed pellet mixed with glucose hydrate Experimental Example 5 of the Invention
PE-alumina mixed pellet

PELLET FOR USE IN SPECTROMETRY, METHOD OF PREPARING THE SAME, AND METHOD OF SPECTROMETRY

TECHNICAL FIELD

The present invention relates to a pellet for retaining a desired sample in spectrometry of the sample. The invention also relates to a method of preparing such a pellet, as well as a method of spectrometry using such a pellet.

BACKGROUND ART

In the field of infrared spectroscopy, a KBr (potassium bromide) tablet method is frequently used, as disclosed in Patent Documents 1 and 2. In the KBr tablet method, initially, a desired solid sample in the form of powder or thin film is retained by a pellet prepared by compression-molding potassium bromide powder. Then, the pellet retaining the sample is irradiated with light, whereby a transmission spectrum or an absorption spectrum is obtained. Since potassium bromide easily transmits infrared light having a wave number of not less than 500 $cm^{-1}$, potassium bromide is suitable for spectrometry in this band. In spectrometry in a band including wave numbers of not less than 250 $cm^{-1}$, cesium iodide is often used as a material for the pellet.

In recent years, spectrometry utilizing terahertz waves, which are the waves in a lower wave number band than the above-described band including a wave number of 250 $cm^{-1}$, is gaining attention and being studied. It is considered that this terahertz spectrometry can detect absorption due to intermolecular interaction, hydrogen bond and Van der Waals force and hence provide characteristic information which cannot be obtained by spectrometry in other wave number bands. However, the transmittances of potassium bromide and cesium iodide with respect to terahertz waves of such a low wave number band are low.

Conventionally, therefore, pellets prepared by compression-molding polyethylene powder are actually used in the terahertz wave spectrometry. Since polyethylene pellets have higher transmittances with respect to terahertz waves than potassium bromide pellets or cesium iodide pellets, the use of polyethylene pellets is preferable for obtaining proper spectrum data.

However, the use of such a polyethylene pellet has the following drawbacks.

Taking glucose as an example, there are two forms of glucose, which are a hydrate, i.e., combined with water molecules, and an anhydride, i.e., not combined with water molecules. When a glucose hydrate is subjected to spectrometry as a sample, a spectrum influenced by water molecules is obtained which is different from a spectrum of an anhydride. Since terahertz waves are easily influenced by water molecules, the difference between the spectrum of a hydrate and that of an anhydride is noticeable in this wave number band.

As will be understood from the above-described example of glucose, even from basically the same substance, different spectrum data is obtained depending on whether the substance is a hydrate or an anhydride. Further, even from samples both of which are hydrates, the spectrum data differs due to the difference in water content therebetween. For this reason, the process for identifying a sample based on the spectrum data is complicated and difficult. Therefore, such problems need to be solved.

Patent Document 1: JP-A-5-232018
Patent Document 2: JP-A-11-166891

DISCLOSURE OF THE INVENTION

Problems to be Solved by the Invention

An object of the present invention is to provide a pellet for use in spectrometry which is capable of solving or alleviating the above-described problems, a method of preparing such a pellet and a method of spectrometry.

Means for Solving the Problems

To solve the above-described problems, the present invention takes the following technical measures.

According to a first aspect of the present invention, there is provided a pellet for use in spectrometry for retaining a sample to be subjected to spectrometry. The pellet includes a first powder of a light transmitting material in a compression-molded form. A second powder which is hydrophilic and water-insoluble is dispersedly mixed in the first powder.

Preferably, the sample is a solid in a powdery form and dispersedly mixed in the first and the second powders.

Preferably, the sample is a solid in a thin film form, and the first and the second powders surround the sample.

Preferably, when the sample is a solution, the pellet is capable of retaining the solution by at least one of an action of the solution to penetrate into the first and the second powders and an action to receive the solution at a surface portion.

Preferably, the first powder comprises at least one of a powder of an olefin resin like polyethylene or polypropylene and a powder of a fluororesin like fluorinated ethylene.

Preferably, the second powder comprises at least one of powders of silica, alumina, titanium dioxide, calcium carbonate and talc.

Preferably, the second powder is smaller than the first powder in average particle size.

According to a second aspect of the present invention, there is provided a method of spectrometry. The method includes the steps of irradiating a pellet for use in spectrometry, which retains a sample, with light, and detecting the light having passed through the pellet to obtain transmission spectrum data or absorption spectrum data on the sample in a predetermined wave number band. The pellet includes a first powder of a light transmitting material in a compression-molded form, and a second powder which is hydrophilic and water-insoluble is dispersedly mixed in the first powder.

Preferably, the method of spectrometry further includes the step of supplying moisture into the pellet and then obtaining transmission spectrum data or absorption spectrum data on the sample when the sample is determined to be an anhydride.

According to a third aspect of the present invention, there is provided a method of preparing a pellet for use in spectrometry. The method includes the steps of mixing a first powder of a light transmitting material with a second powder which is hydrophilic and water-insoluble, and compression-molding the mixture of the first powder and the second powder.

Other features and advantages of the present invention will become more apparent from the detailed description of embodiments given below with reference to the accompanying drawings.

BEST MODE FOR CARRYING OUT THE INVENTION

Preferred embodiments of the present invention are described below with reference to the accompanying drawings.

Figure 1:
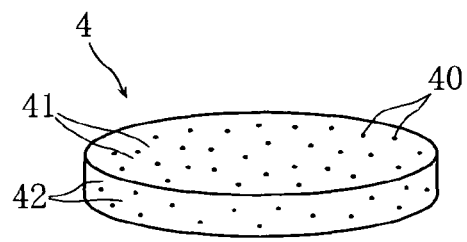
FIG. 1 is a perspective view illustrating an exemplary pellet for use in spectrometry according to the present invention.

FIG. 1 illustrates an exemplary pellet for use in spectrometry according to the present invention. The pellet 4 of this embodiment has a structure formed by mixing a silica ($SiO_2$) powder 42 and a sample 40 in the form of powder into a polyethylene powder 41 as a main material and compression-molding the mixture into a flat disc shape having a thickness of about 1 to 2 mm.

The polyethylene powder 41 is an example of the first powder defined by the present invention. The polyethylene powder 41 is hydrophobic and serves as a diluent for the sample 40. It is preferable that the polyethylene powder 41 has a minute particle size. This is because, as the particle size becomes smaller, scattering of terahertz waves, which is a cause of an error, decreases, thus leading to more precise measurement of terahertz wave absorptivity. The average particle size of the powder 41 is not more than 35 μm, for example.

The silica powder 42 is an example of the second powder defined by the present invention. The silica powder 42 is hydrophilic and water-insoluble. The silica powder 42 has a function to dehydrate the sample 40. It is preferable that the silica powder 42 has a small particle size, similarly to the polyethylene powder 41. More preferably, the average particle size of the silica powder 42 is smaller than that of the polyethylene powder 41. When a fixed amount of the silica powder 42 is mixed in the polyethylene powder 41, silica powder having a smaller particle size has a larger total surface area and hence exhibits a higher dehydration effect on the sample 40 than silica powder having a larger particle size. This also means that the amount of the silica powder 42 to be mixed in the pellet 4 can be reduced. When the mixing amount of the silica powder 42 is reduced, the absorption of terahertz waves by the powder 42 is also reduced, so that the light transmittance of the entire pellet 4 can be enhanced. As the sample 40, various kinds of materials can be used. The sample 40 is pulverized into powder by using e.g. an agate mortar.

The pellet 4 can be prepared by mixing the above-described polyethylene powder 41, silica powder 42 and powdered sample 40 together and compressing the mixture by using a tablet molding machine. The mixing ratio by weight of the polyethylene powder 41 to the silica powder 42 is in the range of about 80:20 to 60:40, for example. The mixing ratio by weight of the total of the powders 41 and 42 to the sample 40 is about 100:3. However, the present invention is not limited to these mixing ratios.

Figure 2:
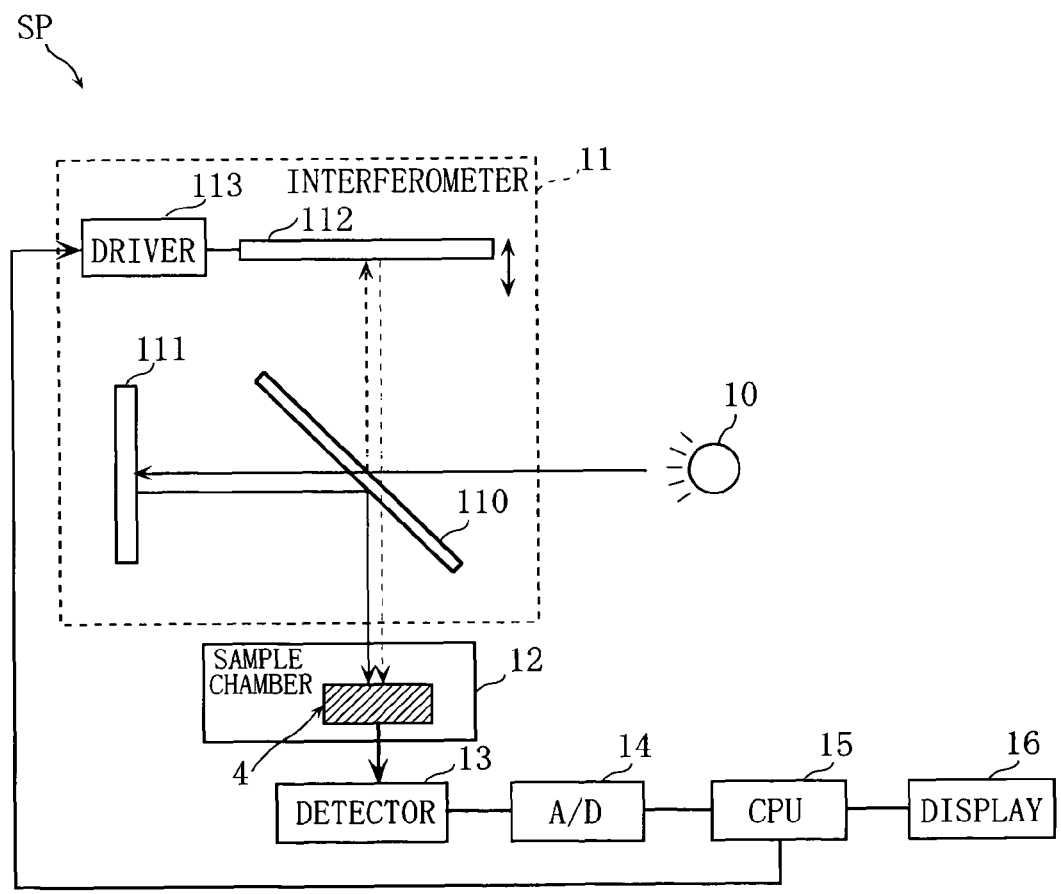
FIG. 2 is a view schematically illustrating an exemplary analysis apparatus used in a method of spectrometry according to the present invention.

The spectrometry using the pellet 4 can be performed using a conventionally known spectrometer. For instance, a spectrometer SP illustrated in FIG. 2 may be used. The spectrometer SP is a Fourier transform spectrometer, which is capable of performing spectrometry in a terahertz wave band. The spectrometer SP includes a light source 10, an interferometer 11, a sample chamber 12, a detector 13, an A/D converter 14, a computer 15 and a display 16.

The light source 10 emits light including a wave number band from e.g. 3 to 630 $cm^{-1}$. The interferometer 11, which is e.g. a Michelson interferometer, splits light traveling from the light source 10 into transmitted light and reflected light by means of a beam splitter 110. The transmitted light reciprocates between the beam splitter 110 and a fixed mirror 111 and then travels toward the sample chamber 12. On the other hand, the reflected light reciprocates between the beam splitter 110 and a movable mirror 112 and then travels toward the sample chamber 12. A driver 113 moves the movable mirror 112 along the optical axis of the reflected light. Thus, the transmitted light and the reflected light have an optical path difference and form coherent light when combined together. The above-described pellet 4 is set in the sample chamber 12. The detector 13 detects the coherent light having been applied from the interferometer 11 to the sample chamber 12 and passed through the pellet 4. The detection signal is AD-converted by the A/D converter 14 and then inputted to the computer 15. The computer 15 is capable of performing Fourier transformation regarding the inputted signal to obtain transmission spectrum data and causing the display 16 to display the waveform. The computer 15 has stored therein spectrum data on various substances as a library and is capable of carrying out a process for e.g. identifying the sample by checking the spectrum data on the sample 40 (data excluding the spectra of the polyethylene powder 41 and the silica powder 42 as the background) against the data in the library.

The advantages of the pellet 4 are described below.

The silica powder 42 is hydrophilic and includes a hydrophilic group at the surface of each particle. Accordingly, in the case where the sample 40 is a hydrate having a water molecule bond structure, the water molecules are released from the water molecule bond structure and bonded to the hydrophilic groups of the silica powder 42. As a result, the sample 40 is dehydrated to become an anhydride. Thus, spectrum data on the sample 40 dehydrated in a relatively short period of time is obtained. When the sample 40 remains a hydrate, the spectrum is influenced by water molecules, and the influence is significant particularly in the terahertz wave band. It is often difficult to identify the sample 40 based on the spectrum significantly influenced by water molecules. According to the present embodiment, by contrast, the sample 40 is dehydrated early so that stable spectrum data inherent to the sample 40 as an anhydride is obtained early, which ensures easy and quick identification of the sample 40.

In the case where the sample 40 is an anhydride from the first, identification processing or the like can be performed directly from the spectrum of the sample 40 in a conventional manner. Since the silica powder 42 transmits terahertz waves relatively easily, the presence of the silica powder 42 does not make the spectrometry difficult in the terahertz wave band.

The pellet 4 can be used also for checking the history of the sample 40, as described below. When the inside of the pellet 4 is dry and the sample 40 is determined to be an anhydride, moisture is supplied into the pellet 4. Specifically, the supply of moisture is achieved by dropping water onto or feeding water vapor into the pellet 4. After moisture is supplied, change in the spectrum of the sample 40 with time is observed.

When the sample 40 is an anhydride from the first, the spectrum of the sample 40 does not change largely in its basic waveform, although the absorbance changes in a wide wave number band with the lapse of time. By contrast, when the sample 40 is originally a hydrate, the sample 40 changes to a hydrated state with the lapse of time, and the spectrum of the sample 40 shows a waveform characteristic of a hydrate which is not observed in the case of an anhydride. Thus, based on the difference in waveform between the spectra, it can be determined whether or not the sample 40 is originally a hydrate. Such determination is useful for identifying the sample 40 more precisely.

FIGS. 3 to 11 illustrate experimental examples using pellets for use in spectrometry according to the present invention and pellets for comparison. The details of the experimental examples are described below.

COMPARATIVE EXAMPLE

Corresponding to Conventional Art

Figure 3:
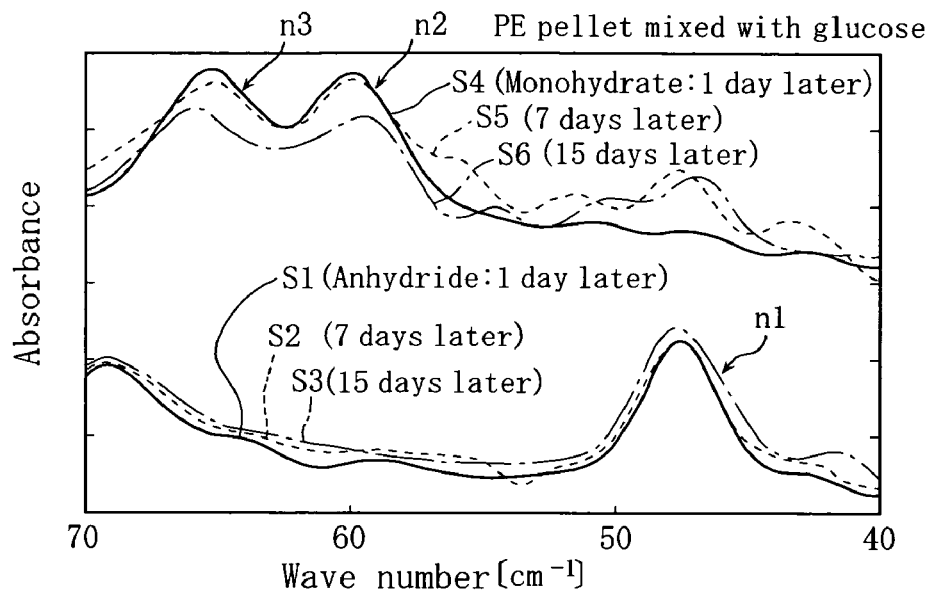
FIG. 3 is a chart illustrating experimental data on a comparative example for comparison with the present invention.

FIG. 3 illustrates experimental data obtained by using a conventional pellet. Specifically, a pellet used in this experiment was prepared by mixing a polyethylene powder having an average particle size of 7 to 9 μm with a glucose powder as a sample and then compression-molding the mixture. The pellet does not contain silica powder. The concentration of glucose is 5%. Spectra S1, S2 and S3 are absorption spectra of a glucose anhydride. (These spectra exclude background absorption spectra. This holds true for other experimental data given below.) Specifically, the spectra S1, S2 and S3 are the data obtained a day after the preparation of the pellet, the data obtained seven days after the preparation of the pellet, and the data obtained fifteen days after the preparation of the pellet, respectively. On the other hand, spectra S4, S5 and S6 are absorption spectra of a glucose monohydrate. Similarly to the above, the spectra S4, S5 and S6 are the data obtained a day after the preparation of the pellet, the data obtained seven days after the preparation of the pellet, and the data obtained fifteen days after the preparation of the pellet, respectively. During these periods of time, the pellet was stored by using a desiccator to minimize the influence of moisture in the air or the like on the pellet.

The spectra S1 to S3 have an absorption peak characteristic of a glucose anhydride in a band around a wave number of 48 $cm^{-1}$, as indicated by reference sign n1. However, substantially no change with time is observed in this part of the spectra. By contrast, the spectrum S4 has two absorption peaks characteristic of a glucose monohydrate in a wave number band from 58 to 65 $cm^{-1}$, as indicated by reference signs n2 and n3. Such absorption peaks are observed also in the spectra S2 and S3, which are the spectrum obtained seven days after the preparation of the pellet and the spectrum obtained fifteen days after the preparation of the pellet, respectively. As will be understood from these, the glucose monohydrate is not sufficiently dehydrated in this experiment.

EXPERIMENTAL EXAMPLE 1 OF THE INVENTION

Figure 4:
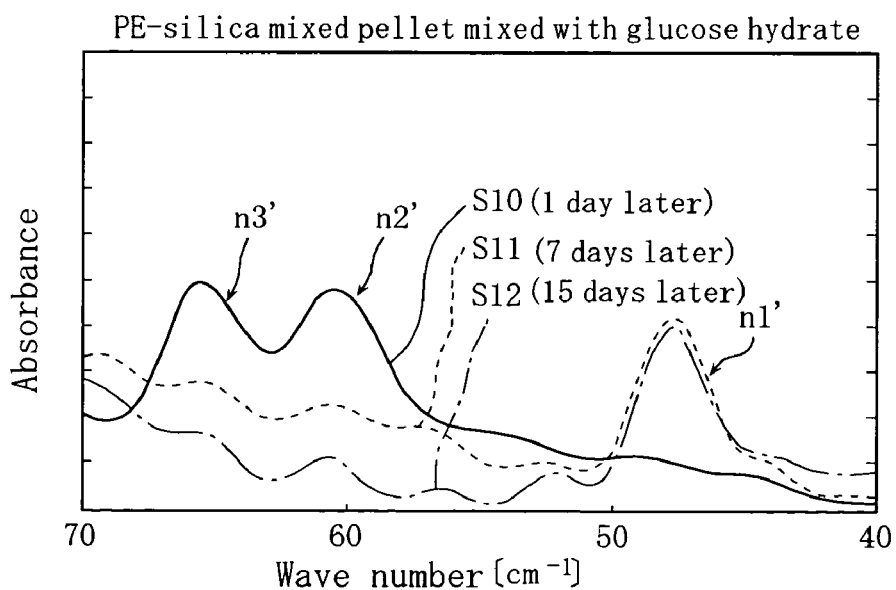
FIG. 4 is a chart illustrating data on experimental example 1.

FIG. 4 illustrates absorption spectra of glucose obtained by using a pellet blended with a silica powder. Specifically, the pellet used in this experiment was prepared by mixing a polyethylene powder having an average particle size of 7 to 9 μm, a silica powder having an average particle size of 7 nm and a glucose monohydrate powder together and then compression-molding the mixture. The mixing ratio by weight of polyethylene to silica is 80:20, and the concentration of glucose in the entirety of the pellet is 5%.

Spectrum S10 is the absorption spectrum of the glucose monohydrate obtained a day after the preparation of the pellet. As indicated by reference signs n2' and n3', the spectrum still has absorption peaks characteristic of a glucose monohydrate. Spectra S11 and S12 are the absorption spectra of the glucose obtained seven days after the preparation of the pellet and fifteen days after the preparation of the pellet, respectively. The absorption peaks characteristic of a glucose monohydrate, indicated by the reference sign n2' and n3', are not observed in the spectra S11 and S12. Further, the spectra S11 and S12 each have an absorption peak characteristic of a glucose anhydride, as indicated by reference sign n1'. Therefore, this experiment proves that the glucose monohydrate was dehydrated almost sufficiently after the lapse of about seven to fifteen days. The experimental data thus obtained also proves that the pellet according to the present invention can exert the effect of actively dehydrating a hydrate.

EXPERIMENTAL EXAMPLES 2 AND 3 OF THE INVENTION

Figure 5:
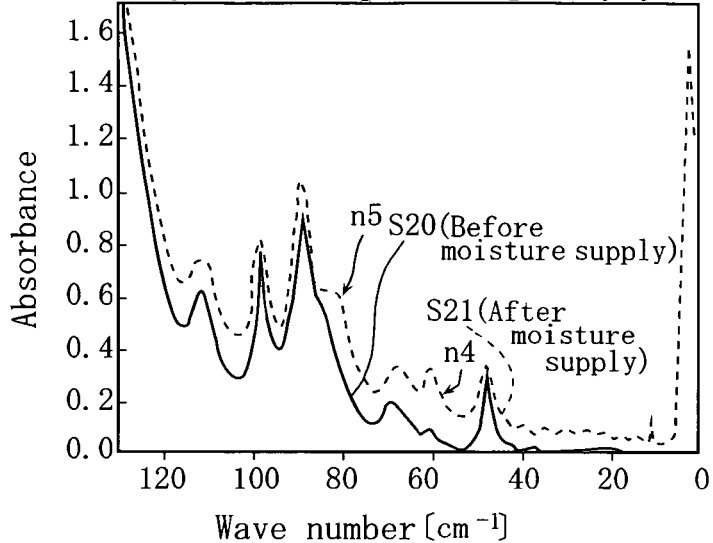
FIG. 5 is a chart illustrating data on experimental example 2.
Figure 6:
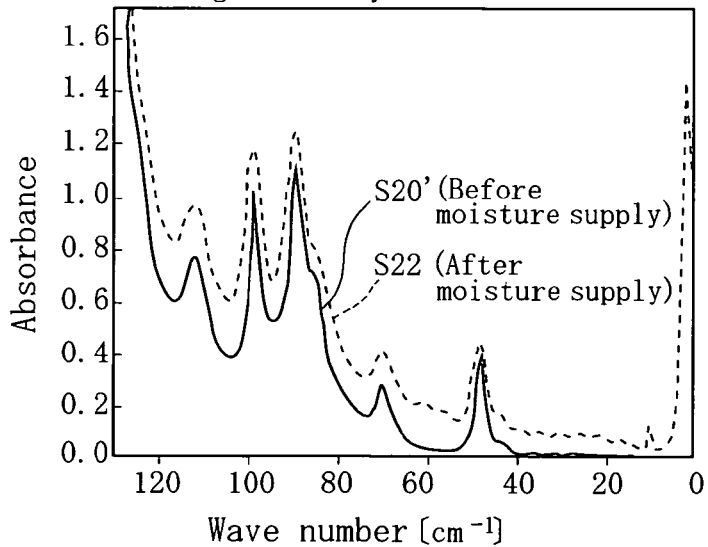
FIG. 6 is a chart illustrating data on experimental example 3.

FIGS. 5 and 6 each illustrate data obtained through an experiment in which a pellet mixed with a glucose powder was supplied therein with water and then dried naturally. Specifically, the pellet used in Experimental Example 2 illustrated in FIG. 5 was the same as that used in Experimental Example 1. The glucose mixed in the pellet had originally been a hydrate. However, the glucose was already dehydrated or the dehydration of the glucose was promoted before the start of the experiment. The water supply to the pellet was achieved by dropping an appropriate amount of water onto the pellet.

In FIG. 5, spectrum S20 is the absorption spectrum of the glucose obtained before the water supply to the pellet, whereas spectrum S21 is the absorption spectrum obtained one and a half hour after the water supply. The spectrum S21 has characteristic waveform portions indicated by reference signs n4 and n5, which are not observed when the glucose is an anhydride.

Unlike Experimental Example 2, Experimental Example 3 illustrated in FIG. 6 used a pellet mixed therein with a glucose anhydride which did not have a history of change from a hydrate to an anhydride. The pellet contains a silica powder in addition to a polyethylene powder. The mixing ratio among polyethylene, silica and glucose anhydride is substantially equal to that in Experimental Example 2. Similarly to the spectrum 20 in FIG. 5, spectrum S20' in FIG. 6 is the absorption spectrum of the glucose obtained before the water supply to the pellet. Spectrum S22 is the absorption spectrum obtained one and a half hour after the water supply. The spectrum S22 on the whole shows a higher absorbance than that of the spectrum S21, but does not have characteristic waveforms like those indicated by the reference signs n4 and n5 in FIG. 5.

It will be understood from Experimental Examples 2 and 3 that, when water is supplied to pellets according to the present invention and their spectra are checked thereafter, different spectra are obtained from a sample which was once a hydrate and a sample which has never been a hydrate. Thus, whether the sample is originally a hydrate or not can be determined based on the difference in spectrum, which makes it possible to identify a sample more precisely.

EXPERIMENTAL EXAMPLE 4 OF THE INVENTION

Figure 7:
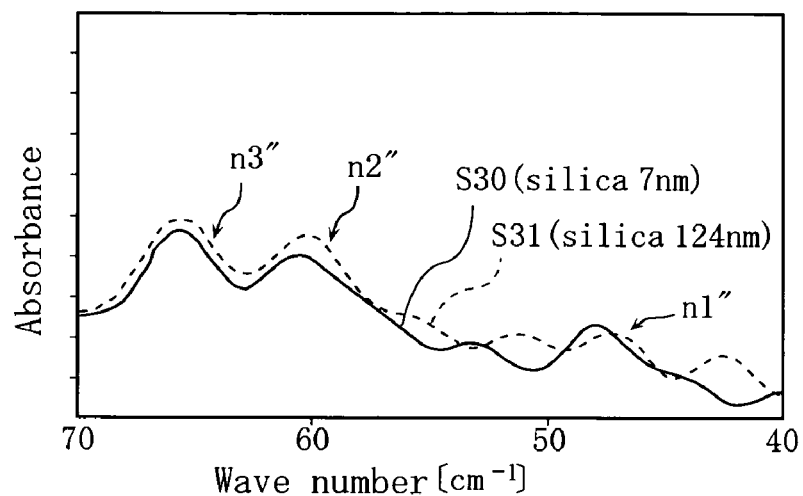
FIG. 7 is a chart illustrating data on experimental example 4.

FIG. 7 illustrates data on spectrometry using silica powders of different particle sizes. Specifically, similarly to the pellet used in Experimental Example 1, a pellet mixed therein with a glucose monohydrate (average particle size of silica: 7 nm), and spectrometry was performed three days later, whereby absorption spectrum S30 of the glucose was obtained. On the other hand, a similar pellet was prepared with silica having an average particle size of 124 nm (this pellet was the same as the above-described pellet except the particle size of silica), and spectrometry was performed three days later, whereby absorption spectrum S31 was obtained.

As compared with the spectrum S31, the spectrum S30 shows a lower absorbance at the portions indicated by reference signs n2″ and n3″, which are the portions characteristic of a glucose hydrate, and a slightly higher absorbance peak at the portion indicated by reference sign n1″, which is characteristic of a glucose anhydride. As will be understood from this experiment, basically, a silica powder having a smaller particle size accelerates dehydration of glucose further. Though not particularly shown as data, the inventors of the present invention further performed an experiment using silica powders of various particle sizes other than those noted above. As a result, it was found that, when silica powders of different particle sizes were similar in shape to each other, e.g. a spherical shape, a silica powder having a smaller particle size tended to be more suitable for accelerating dehydration of a sample. In the present invention, however, the silica powder (the second powder) does not need to be spherical. This holds true for the first powder. A powder comprising non-spherical particles, such as those which have irregular surfaces or which are entirely flat, has a larger surface area than a powder comprising spherical particles when the particle sizes of these powders are substantially the same. Thus, the use of a powder comprising non-spherical particles as the second powder is more suitable for accelerating dehydration of a sample while reducing the amount of the second powder.

EXPERIMENTAL EXAMPLES 5-8 OF THE INVENTION

FIGS. 8 to 11 each illustrate data obtained by using a water-insoluble hydrophilic material other than silica as the second powder defined by the present invention. Specifically, FIGS. 8, 9, 10 and 11 illustrate spectral waveforms obtained by using different kinds of pellets containing an alumina powder (average particle size: 12 nm), a titanium dioxide powder (average particle size: 21 nm), a calcium carbonate powder (average particle size: 80 nm) and a talc powder (average particle size: 2.5 μm), respectively, which were mixed with a polyethylene powder and a glucose monohydrate powder. In each of these figures, the solid line depicts the absorption spectrum of glucose measured a day after the preparation of the pellet, the broken line depicts the absorption spectrum of glucose measured seven days after the preparation of the pellet, and the dash-dotted line depicts the absorption spectrum of glucose measured fifteen days after the preparation of the pellet. The pellets used in these experiments had the same structure as that of the pellet used in Experimental Example 1 except the material of the second powder.

Figure 8:
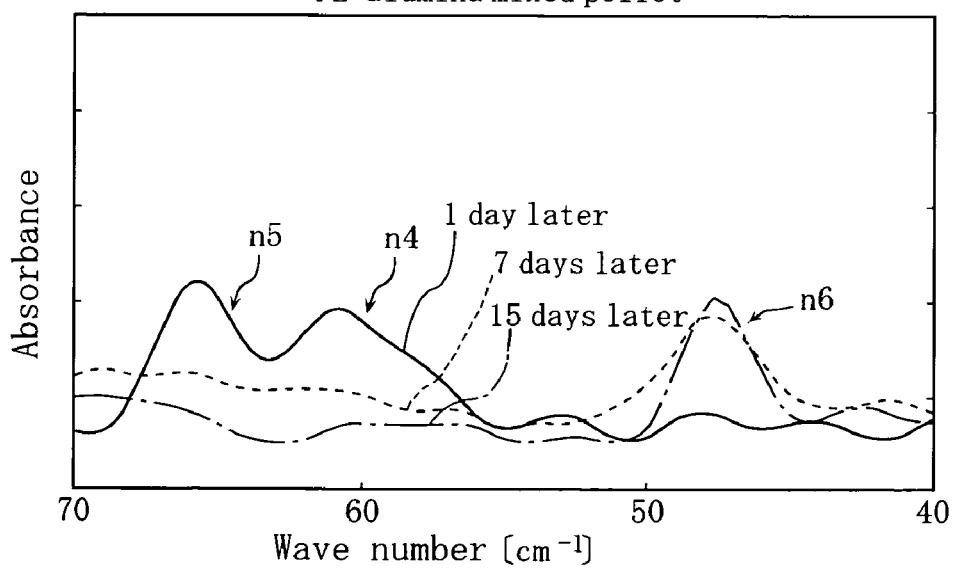
FIG. 8 is a chart illustrating data on experimental example 5.
Figure 9:
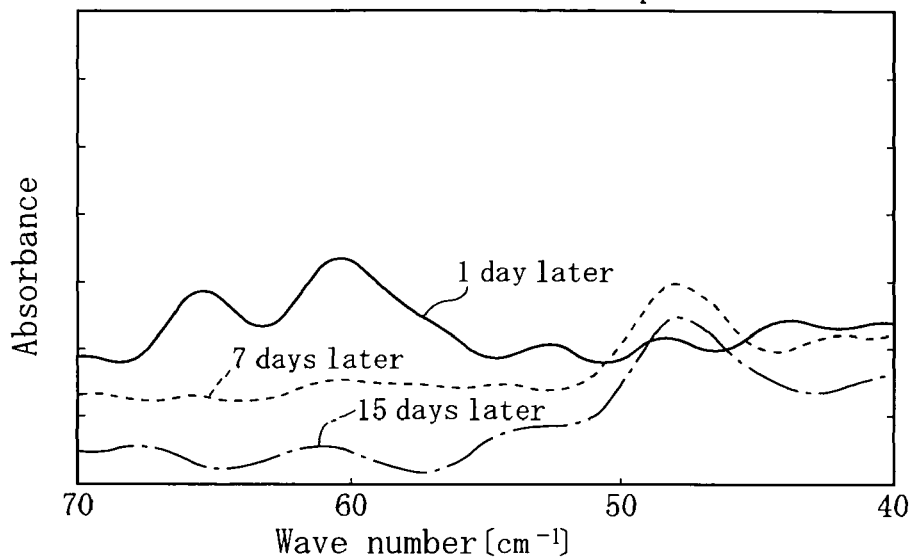
FIG. 9 is a chart illustrating data on experimental example 6.
Figure 10:
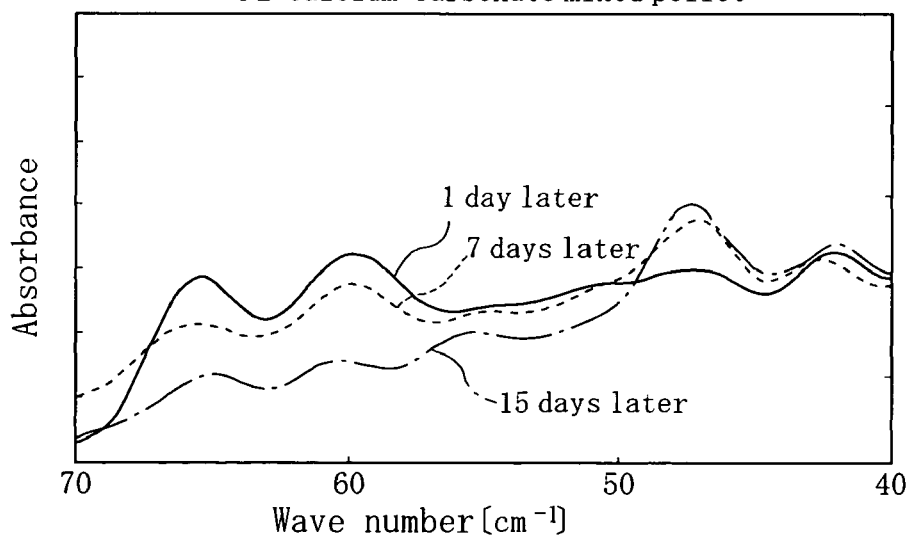
FIG. 10 is a chart illustrating data on experimental example 7.
Figure 11:
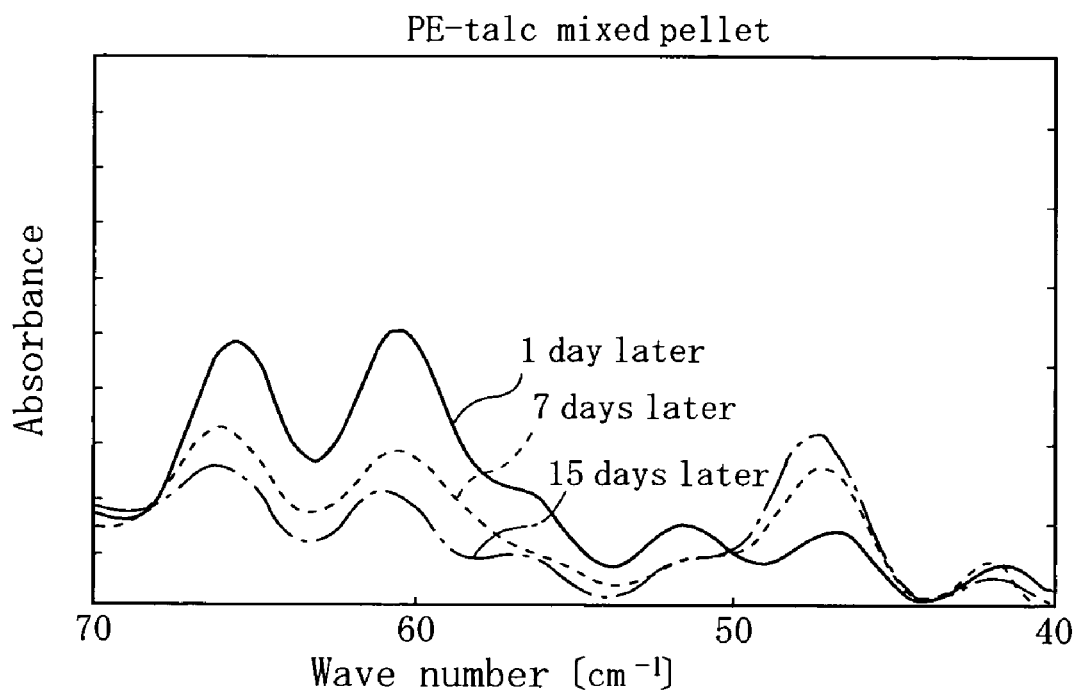
FIG. 11 is a chart illustrating data on experimental example 8.

In FIG. 8, the spectrum of the sample obtained a day after the preparation of the pellet has waveforms characteristic of a glucose monohydrate, as indicated by reference signs n4 and n5. In the spectra obtained seven days after and fifteen days after the preparation of the pellets, such waveforms are not observed, but instead, a waveform characteristic of a glucose anhydride is observed, as indicated by reference sign n6. As can be seen from this experiment, dehydration of glucose proceeds even when alumina is used instead of silica. The phenomenon similar to that obtained by the use of alumina is also observed in the data illustrated in FIGS. 9 to 11. This indicates that the effect of dehydrating glucose is obtained even when titanium dioxide, calcium carbonate or talc is used.

According to the data on the experiments 5 to 8, it is found that materials other than the above can be used widely as the second powder of the present invention as long as the materials are hydrophilic and water-insoluble. Thus, as the second powder, various materials other than the above can be employed widely. In the present invention, even a material which is not originally hydrophilic can be used as the second powder in the case where the material has been subjected to hydrophilicity-imparting treatment to have a hydrophilic surface. However, as the second powder, it is preferable to select a material which has a high transmittance with respect to light used in the spectrometry and does not considerably impair the light transmitting property of the pellet. From this point of view, in addition to silica described above, alumina, titanium dioxide, calcium carbonate and talc, which have relatively high transmittances with respect to terahertz waves, are preferable materials. The second powder defined by the present invention is not limited to a single kind of material, but two kinds of powder, e.g. silica powder and alumina powder, may be mixed in a pellet. This holds true for the first powder.

Figure 12:
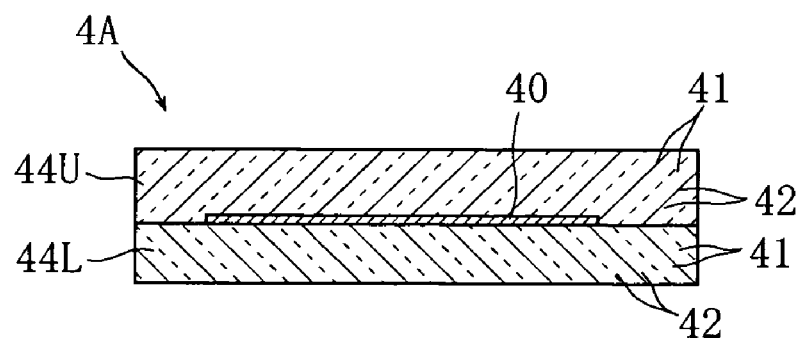
FIG. 12 is a sectional view illustrating another exemplary pellet for use in spectrometry according to the present invention.

FIG. 12 illustrates another exemplary pellet for use in spectrometry according to the present invention.

The pellet 4A illustrated in FIG. 12 includes an upper half portion 44U and a lower half portion 44L which are superposed on each other, and a sample 40 in the form of thin film (in a film form) sandwiched and confined between the upper and the lower half portions. The upper half portion 44U and the lower half portion 44L are each prepared by compression-molding a mixture of a polyethylene powder 41 and a silica powder 42, for example.

The pellet 4A of this embodiment is formed as a so-called window plate for sandwiching and supporting the sample 40. Since the sample 40 is formed into a thin film, transmission of a certain amount of light in the spectrometry process is secured. In the pellet 4A again, the silica powder 42 can be placed adjacent to the sample 40. By so doing, the pellet 4A is expected to have the effect of accelerating dehydration of the sample 40 when the sample is a hydrate.

Figure 13:
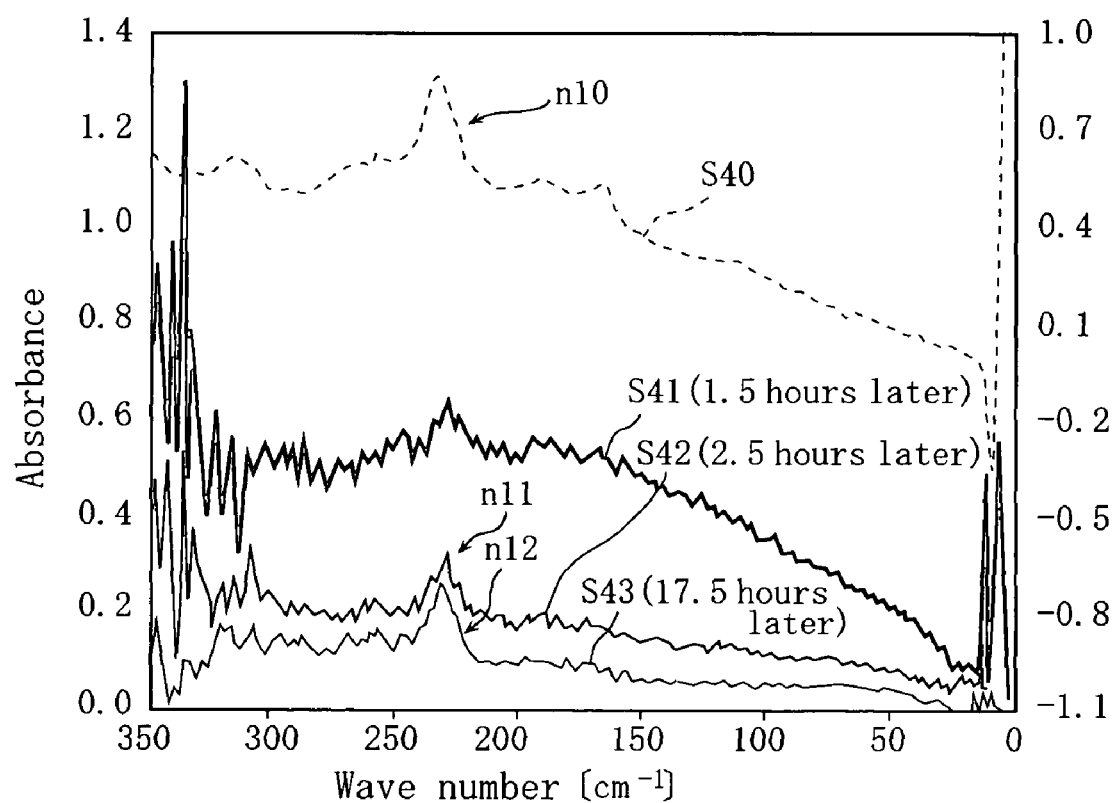
FIG. 13 is a chart illustrating data on experimental example 9.

FIG. 13 illustrates data on an experiment (Experimental Example 9) in which a solution containing a sample is dropped onto a pellet before spectrometry. The pellet used in this experiment had the same structure as that used in Experimental Example 1 except that the pellet used in this experiment did not contain a solid sample. A solution (3% concentration) of red pigment No. 105 (sodium salt) legally prescribed in Japan in ethanol was dropped onto the pellet, and spectrometry was performed during a process in which the pellet was allowed to dry naturally. The data of FIG. 13 includes a relatively large amount of noise in a wave number band around 0 cm$^{-1}$ and a wave number band around 350 cm$^{-1}$.

Spectrum S40 in FIG. 13 is the absorption spectrum inherent to the above-described pigment. Spectra S41, 42 and 43 are the absorption spectra obtained one and a half hour after the dropping of the ethanol solution, two and a half hours after the dropping of the ethanol solution and seventeen and a half hours after the dropping of the ethanol solution, respectively. The spectra S42 and S43, which are the spectra obtained in the stage where natural drying of the pellets has proceeded to a considerable extent, show waveforms corresponding to the absorption peak of the spectrum S40 indicated by reference sign n10 at portions indicated by reference signs n11 and n12.

As will be understood from the data on this experiment, the pellet for use in spectrometry according to the present invention can also be used in such a manner that a sample in the form of a solution is dropped onto the surface of the pellet. By allowing the solvent to evaporate off after the dropping of the solution, the solute can be retained on the pellet. As the mode of retainment of the solution by the pellet, there are two conceivable modes, i.e., the solution is retained by its penetration into the pellet or the solution is retained as received and remaining on the surface of the pellet without such penetration. The both modes are possible in the present invention.

The present invention is not limited to the foregoing embodiments.

Although polyethylene, which has a high transmittance with respect to terahertz waves, is preferable as the first powder defined by the present invention, the present invention is not limited to polyethylene. The first powder may comprise any other olefin resin such as polypropylene or a fluororesin such as tetrafluoroethylene, because they have preferable transmittances with respect to terahertz waves. Materials other than the foregoing materials may be employed as the first powder. The pellet for use in spectrometry according to the present invention may contain, in addition to the first powder and the second powder, a third powder comprising a material which is different from those of the first and the second powders. There is no limitation on the mixing ratio of the first and the second powders.

The invention claimed is:

1. A pellet for use in spectrometry for retaining a sample to be subjected to spectrometry, comprising: a first powder of a light transmitting material in a compression-molded form, wherein a second powder which is hydrophilic and water-insoluble is dispersedly mixed in the first powder.

2. The pellet for use in spectrometry according to claim 1, wherein the sample is a solid in a powdery form and dispersedly mixed in the first and the second powders.

3. The pellet for use in spectrometry according to claim 1, wherein the sample is a solid in a thin film form, and the first and the second powders surround the sample.

4. The pellet for use in spectrometry according to claim 1, wherein, when the sample is a solution, the pellet is capable of retaining the solution by at least one of an action of the solution to penetrate into the first and the second powders and an action to receive the solution at a surface portion.

5. The pellet for use in spectrometry according to any one of claims 1 through 4, wherein the first powder comprises at least one of a powder of an olefin resin and a powder of a fluororesin.

6. The pellet for use in spectrometry according to claim 5, wherein the powder of the olefin resin is at least one of polyethylene and polypropylene, and wherein the powder of the fluororesin is fluorinated ethylene.

7. The pellet for use in spectrometry according to claim 1, wherein the second powder comprises at least one of powders of silica, alumina, titanium dioxide, calcium carbonate and talc.

8. The pellet for use in spectrometry according to claim 1, wherein the second powder is smaller than the first powder in average particle size.

9. A method of spectrometry comprising the steps of:
   irradiating a pellet for use in spectrometry, which retains a sample, with light; and
   detecting the light having passed through the pellet to obtain transmission spectrum data or absorption spectrum data on the sample in a predetermined wave number band;
   wherein the pellet comprises a first powder of a light transmitting material in a compression-molded form, a second powder which is hydrophilic and water-insoluble being dispersedly mixed in the first powder.

10. The method of spectrometry according to claim 9, further comprising the step of supplying moisture into the pellet and then obtaining transmission spectrum data or absorption spectrum data on the sample when the sample is determined to be an anhydride.

11. method of preparing a pellet for use in spectrometry, the method comprising the steps of:
    mixing a first powder of a light transmitting material with a second powder which is hydrophilic and water-insoluble; and
    compression-molding the mixture of the first powder and the second powder.

* * * * *